United States Patent [19]

Ward et al.

[11] Patent Number: 4,716,236

[45] Date of Patent: Dec. 29, 1987

[54] METHOD FOR SYNTHESIZING ESTERS

[75] Inventors: Frederick E. Ward; Kin F. Yip, both of Elkhart, Ind.

[73] Assignee: Miles Laboratories, Inc., Elkhart, Ind.

[21] Appl. No.: 805,254

[22] Filed: Dec. 5, 1985

Related U.S. Application Data

[63] Continuation of Ser. No. 597,337, Apr. 6, 1984, abandoned.

[51] Int. Cl.$^4$ .......................................... C07D 207/36
[52] U.S. Cl. ................................................... 548/556
[58] Field of Search .............................. 548/541, 556

[56] References Cited

U.S. PATENT DOCUMENTS 4,278,763 7/1981 Berger et al. ............................ 435/23

FOREIGN PATENT DOCUMENTS 907424 10/1962 United Kingdom ................ 548/541

OTHER PUBLICATIONS

Borgman, et al., "Acetylation of Apomorphine . . . ," Chem. Abst. 83: 59124 K (1975).
McOmie, J. F. W. Protective Groups in Organic Chemistry, Plenum, New York (1973) pp. 44–45.
Greene, Theodora, Protective Groups in Organic Chemistry, John Wiley, New York (1981), pp. 101–103, 106–107.
March, Advanced Organic Chemistry, McGraw-Hill, New York (1977) p. 372.
March, Jerry, Advanced Organic Chemistry, McGraw-Hill, New York (1977), p. 361.

Primary Examiner—Mary E. Ceperley
Attorney, Agent, or Firm—Roger N. Coe

[57] ABSTRACT

A method for preparing an ester having the structure

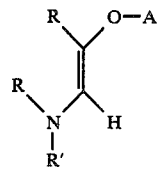

in which A is an acid residue; R, same or different is H, lower alkyl, aryl, or in which both R together form a ring structure and R' is H, lower alkyl or aryl. The method comprises combining a first compound having the structure

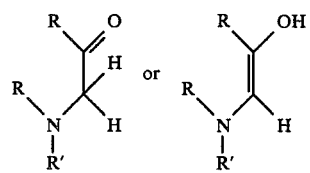

and a second compound which is an acyl halide corresponding to A, said combining being performed in the presence of an organic acid.

6 Claims, No Drawings

METHOD FOR SYNTHESIZING ESTERS

This is a continuation of application Ser. No. 597,337, filed Apr. 6, 1984, now abandoned.

CONTENTS

1. Introduction
2. Background of the Invention
3. Summary of the Invention
4. Definitions
   4.1 Acid Residue
   4.2 Aryl
   4.3 Lower Alkyl
   4.4 Acyl Halides
5. Detailed Description of the Invention
6. Experimental
   6.1 General Information
   6.2 Synthesis of 3-(N-tosyl-L-alaninyloxy)-5-phenylpyrrole
   6.3 Synthesis of 3-(N-tosyl-L-alaninyloxy)-1-methyl-5-phenylpyrrole
   6.4 Synthesis of 3-(N-tosyl-L-alaninyloxy-5-(p-chlorophenylpyrrole)
   6.5 Preparation of indoxyl-N-tosyl-L-alaninate
      6.5.1 Use of Citric Acid
      6.5.2 Use of Oxalic Acid
      6.5.3 Use of Trifluoroacetic Acid
      6.5.4 Use of $CH_2Cl_2$ as Solvent
      6.5.5 Use of Diisopropylethylamine
      6.5.6 Use of Pyridine

1. INTRODUCTION

The present invention relates to the preparation of novel ester compounds useful in assaying a test sample of the presence of analytes such as leukocyte cells, esterase and protease. The invention is particularly useful in detecting leukocyte levels in body fluids such as urine, and reduces the laboratory procedure for such assay from a cumbersome counting procedure requiring microscopic observation, to a rapid, facile dip-and-read operation.

The presence of an abnormally high level of leukocytes in a patient's urine is possibly indicative of such pathological conditions as kidney or urogential tract infection or other dysfunction. Accordingly, accurate urinary leukocyte information can be an invaluable tool to the physician in diagnosis and treatment of such pathologies.

Traditionally, the medical profession has relied on visual determination techniques to count leukocyte population in urine sediment or uncentrifuged urine, a process requiring expensive equipment such as a centrifuge and microscope, as well as inordinate time expenditure in the part of the clinician. Moreover, the traditional techniques suffer from the disadvantage that only intact cells are determined. Leukocytes occurring in the urinary system are subject to conditions which can favor extensive cell lysis. For example, it is known that in urines of abnormally high pH, leukocyte half life can be as low as 60 minutes. Since lysed cells escape detection in visual examination techniques, erroneously low determinations and false negatives can result.

Of the two techniques of microscopic leukocyte analysis—urine sediment and noncentrifuged, homogenized urine—the former is clearly the most desirable. Although dependable results can inure to the latter, urine sediment observation is used in an overwhelming majority of instances. It requires that the urine sample be centrifuged and the sediment isolated and subjected to microscopic inspection. The analyst then counts the number of leukocytes appearing in the viewing field. This task is further complicated by the presence of other urinary components in the sediment such as epithelial cells and salt particles. The varying content of sediment constituents, coupled with other complicating factors including non-homogeneity of the sample and differing optical powers among microscope equipment, can lead to enormous errors in the ultimate determination.

It is thus apparent that a quick, facile methods of leukocyte determination, one which would eliminate the need for time-consuming techniques, as well as cost-consuming equipment, and which would provide accurate responses to esterase, protease or leukocyte cells, whether the cells are intact or lysed, would indeed constitute a quantum advance in the state-of-the-art. The present invention provides such an advance. Moreover, it is based, not on the ability to see leukocytes, but on the enzymatic activity they exhibit, and therefore is substantially free of the inaccuracies described above.

2. BACKGROUND OF THE INVENTION

Traditionally, esterification reaction between acyl halides and alcohols (or phenols) to form esters are carried out in basic media. This is primarily to neutralize the halogen acid (HCl, HF, HBr, etc.) formed by the esterification, thus shifting the equilibrium in favor of the formation of the ester.

In the case where it is desirable to prepare esters of amino alcohols, however, it has been necessary to substitute the amino moiety with an N-blocking group, such as acetyl, tosyl or tert-butyloxycarbonyl. Otherwise the compound becomes acylated both at the hydroxyl and the amine groups. Moreover where the compound is an enolic alcohol o-acylation is hampered by the keto form, and side reactions on the more nucleopholic functional groups are likely to occur.

3. SUMMARY OF THE INVENTION

Briefly stated, the present invention comprises a method for preparing an ester having the structure

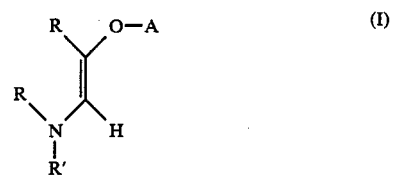

in which
  A is an acid residue
  R, same or different is H, lower alkyl, aryl, or in which both of R together form a ring structure, and
  R' is H, lower alkyl or aryl.

The method comprises combining a first compound having the structure

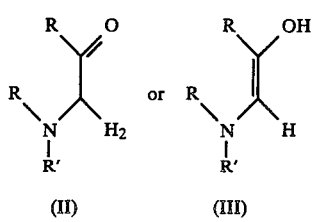

and a second compound which is an acyl halide corresponding to A, said combining being performed in the presence of an organic acid.

4. DEFINITIONS

The following definitions are provided to clarify the scope of the present invention, and to enable its formulation and use.

4.1 The expression "acid residue" includes derivative structures of ester-forming acids without their characteristic acidic —OH group. Thus, the term includes the acids phosphoric, sulfonic, carbonic and carboxylic, i.e.,

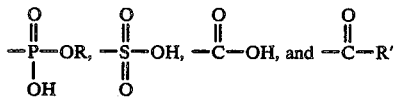

in which R' is defined above.

The expressions "N-blocked-amino acid residue" and "N-blocked-peptide residue" requires definition on two counts. "N-blocked" refers to the chemistry of the amine group of an amino acid or peptide whereby a hydrogen bound to the nitrogen atom is replaced by a protective group such as acetyl, p-toluene-sulfonyl (tosyl) and tert-butyloxycarbonyl (t-BOC) and other N-protective groups known in the art.

By the expressions "amino acid residue" and "peptide residue" is meant an amino acid or peptide molecule without the —OH of its carboxyl group.

4.2 By the expression "aryl" is meant any ring system containing aromaticity. Included by the expression are such 5- and 6-membered rings as pyrrole, phenyl, and pyridyl, as well as fused ring systems such as naphthyl. Thus, the aromatic ring system can be heterocyclic or homocyclic, and can be substitued or unsubstitued, provided the substituent groups(s) not interfere with ability of composition to hydrolyze in the presence of leukocyte cells, esterase or protease. Selection of such substituents is a routine laboratory determination, given the present disclosure.

4.3 The expression "lower alkyl", as used in the present disclosure, is an alkyl moiety containing about 1–6 carbon atoms. Included in the meaning of lower alkyl are methyl, ethyl, n-propyl, isopropyl, n-butyl, sec-butyl, tert-butyl and all isomers of pentyl and hexyl. These can be unsubstituted, or they can be substituted provided any such substituents not interfere with the operation or functioning of the presently claimed composition or test device in its capablility to detect leukocyte cells, esterase or protease.

4.4 The "acyl halides" used in the method of the present invention correspond to A, above. For example, acyl halides included can be sulfonyl chloride, carboxyl chloride, phosphonyl chloride and N-tosyl-L-alaninyl chloride. The preferred halide is chloride.

5. DETAILED DESCRIPTION OF THE INVENTION

The present invention relates generically to esterification of compounds having the structure

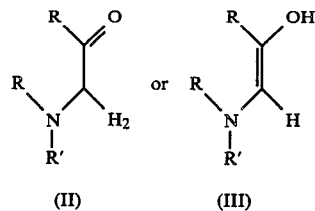

wherein R and R' are as defined above. Included are pyrrole, indole, pyridyl and 2-amino-ketones.

The temperature at which the reaction is conducted should assure the stability of the reactants as well as the product, and thus can be routinely determined on a case-by-case basis. When the starting material, for example, is indoxyl or 3-hydroxy-5-phenylpyrrole, the preferred temperature range is about $-30°$ C. to room temperature. Ideally the reaction is run at about 5° C. for indoxyl and about 0° C. for the pyrrole.

Solvents used for the esterification are non-aqueous, and should be relatively free of trace water. Included as preferred solvents are tetrahydrofuran (THF), methylene chloride, chloroform, acetone, diethyl ether, and benzene. The solvent most preferred is THF.

Other reagents which affect the reaction catalytically can also be employed. Illustrative of these are pyridine, and 2,6-lutidine and other weak organic bases. Materials which assure anhydrous conditions, such as anhydrous $MgSO_4$ and molecular sieves can also be added to the reaction mixture.

The organic acid which is an essential part of the invention process possesses wide latitude in its definition. It includes alkanoic acids, substituted alkanoic acids, aromatic carboxylic acids and substituted aromatic carboxylic acids. Specific compounds included within the scope of "organic acid" include trifluoroacetic, oxalic, citric, acetic, benzoic, 2,4-dinitrobenzoic methane sulfonic and the like.

6. EXPERIMENTAL

The following examples are provided to further assist the reader in making and using the present invention. Thus, preferred embodiments are described in experimental detail and analyzed as to the results. The examples are meant to be illustrative only, and are in no way intended as limiting the scope of the invention described and claimed herein.

6.1 General Information

In the following experimental discussion abbreviations are used as indicated:

g=gram
kg=kilogram
L=liter
mL=milliliter
M=molar
mM=millimolar
N=normal
eq=equivalents
mol=gram molecular formula (moles)
mmol=gram molecular formula $\times 10^{-3}$ (millimoles)
aq=aqueous hr=hour
TLC=thin layer chromatography Infrared (IR) spectra were obtained with a Perkin-Elmer Model 710B or 237 infrared spectrophotometer as solutions in CHCl$_3$ unless otherwise noted; the 1602 cm$^{-1}$ band of polystyrene film was used as an external calibration standard. Signals are reported as cm$^{-1}$.

Proton magnetic resonance (1H NMR) spectra were obtained at 89.55 MHz using a JEOL FX-900 spectrometer or at 60 MHz using a Varian T-60 spectrometer; spectra were obtained in CDCl$_3$ solution unless otherwise noted. Chemical shifts are reported in parts per million downfield from the internal standard tetramethylsilane.

Carbon-13 magnetic resonance (13C NMR) spectra were obtained at 22.5 MHz using JEOL FX90Q spectrometer with Fourier transform and with full proton broad-band noise decoupling; spectra were obtained in CDCl$_3$ solution unless otherwise noted. Carbon shifts are reported in parts per million downfield from the internal standard tetramethylsilane.

Organic reagents were obtained from Aldrich Chemical Company and were used without purification, unless otherwise noted. Inorganic reagents were ACS reagent grade from Fisher Scientific Company or other major vendor. Reaction solvents were ACS reagent grade; tetrahydrofuran (THF) was HPLC grade from J. T. Baker Chemical Company. Brine refers to a saturated aqueous sodium chloride solution.

Thin layer chromatography (TLC) was performed using silica gel 60F-254 plates from E. Merck. Column chromatography was performed using E. Merck Silica Gel 60 (70-230 mesh). All melting points and boiling points reported are uncorrected.

The following high pressure liquid chromatography (HPLC) procedure was followed.

A HPLC column measuring 250×4.6 mm, charged with silanized silica gel (Partisil obtained from Waters and Associates) having an average particle size of 5 microns. The elutant or mobile phase was a mixture of n-hexane and ethyl acetate (7:3 parts by volume). The flow rate was 1.5 mL per minute at a pressure of 1000 p.s.i. Eluted components were detected using a Varian Aerograph (Varian Associates) reading at a wavelength of 254 nanometers.

In each case, the retention time of purified product was determined, to assure the presence of that product when analyzing the reaction mixtures. The retention time for indoxyl-N-tosyl-L-alaninate was about 9 minutes.

6.2 Synthesis of 3-(N-tosyl-L-alaninyloxy)-5-phenylpyrrole (4)

The synthesis of 3-(N-tosyl-L-alaninyloxy)-5-phenylpyrrole is illustrated in the following reaction sequence

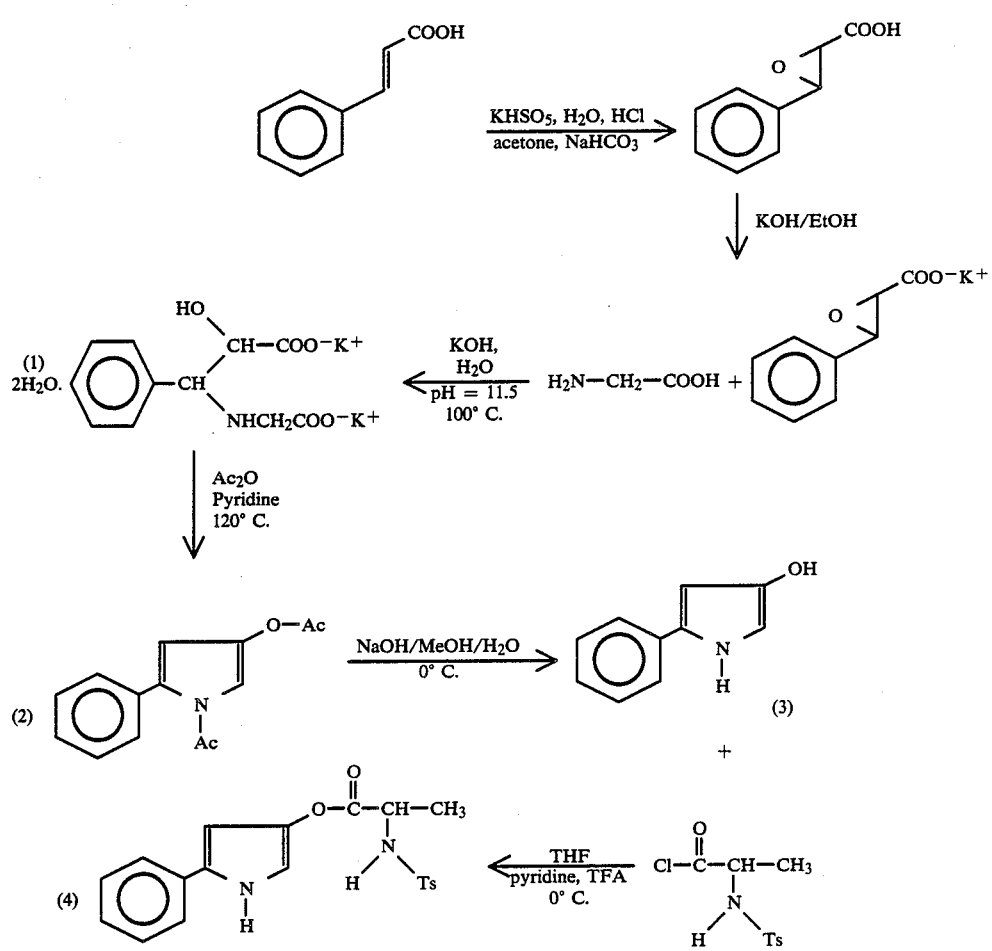

N-tosyl-L-alanine

L-alanine (100 g; 1.11 moles) was dissolved in 2.25 L of 1N sodium hydroxide (aq), cooled to 5° C. and stirred while a solution of p-tolunesulfonyl chloride (218 g;

1.11 moles) dissolved in 450 mL of toluene was added slowly. The mixture was stirred at ambient temperature for 20 hr. The layers were separated and the chilled aqueous layer acidified to pH 1 with concentrated hydrochloric acid. The white solid title compound was collected by filtration, washed with water and dried. Yield 178.5 (66%) mp 134°–5° C. IR (CHCl$_3$) cm$^{-1}$ 1726, 1340, 1165, 1095; 1H NMR (DMSO-D$_6$) δ 1.20 (d, J=7, 3H), 2.40 (s, 3H), 3.85 (p, J=8, 1H), 6.4 (br s, 1H) (CO$_2$H), 7.41 (d, J$_{AB}$=8, 2H) and 7.75 (d, J$_{AB}$=8, 2H) [center of pattern: 7.58; ΔV$_{AB}$=20.49 Hz], 8.03 (br d, J=8, 1H)(NH).

N-tosyl-L-alaninyl chloride

Method A

A mixture of N-tosyl-L-alanine (12.4 g; 0.05 mol) and thionyl chloride (25 ml) was heated for 90 minutes at 55° C., and then concentrated on the rotary evaporator at 40° C. The red solid residue was dissolved in 200 mL of boiling CCl$_4$, decolorized with 20 g of oven-dried Norit® 211 activated carbon (American Norit Co., Inc.), filtered and chilled. The cream colored solid title product was collected by filtration, washed with hexane and dried. Yield 8.48 g (65%) with mp 101°–101.5° C. IR (CHCl$_3$) cm$^{-1}$ 3360, 3260, 3025, 1775, 1605, 1350, 1170, 910; 1H NMR (CDCl$_3$) 1.48 (d, J=7, 3H), 2.43 (s, 3H), 4.33 (p, J=8, 1H), 5.98 (br d, J=8, 1H) (NH), 7.31 (d, J$_{AB}$=8, 2H) and 7.76 (d, J$_{AB}$=8, 2H) [center pattern: 7.53; ΔV$_{AB}$=26.83 Hz].

Anal. Calcd. for C$_{10}$H$_{12}$ClNO$_3$S: C, 45.89; N, 4.62; N, 5.35. Found: C, 46.63; H, 4.90; N, 5.19.

Method B

A mixture of N-tosyl-L-alanine (3.1 g; 13 mmol) and thionyl chloride (6 mL) was heated for 90 min at 50° C., then diluted with 50 mL of dry hexane. The mixture was stirred rapidly, chilled and the solid product filtered. yield 3.15 g (93%) mp 99°–100° C. The IR spectrum was identical to that of the recrystallized material prepared by Method A.

2-Hydroxy-3(carboxymethylamino)-hydrocinnamic acid dipotassium salt dihydrate (1)

A stirred slurry of 1.0 kg of transcinnamic acid (6.75 mol) in 4.5 L acetone was treated first with NaHCO$_3$ (2.47 kg; 29.4 mol; 4.36 eq) then carefully with water (4.5 L). The resulting thick mixture was treated dropwise, over 1.5–2.0 hr, with a solution of OXONE® (DuPont Co.) monopersulfate compound (3.78 kg; contains 1.825 eq of KHSO$_5$) in 0.4 mM aqueous disodium ethylenediamine tetracetic acid (EDTA) (14.5 L; prepared by dissolving 2.17 g disodium EDTA dehydrate in 14.5 L distilled water). [1,2] During this addition the reaction temperature was maintained at 24°–27° C. using a water bath; the reaction pH was noted to be about 7.4. After the addition was completed the mixture was stirred an additional 0.5 hour then cooled to about 10° C. The reaction was acidified with conc. HCl (~1.2 L) to pH=2 while maintaining the temperature at around 10° C., and then treated with CH$_2$Cl$_2$ (5.05 L) and stirred vigorously for 10 minutes.

[1]. J. O. Edwards, et al, Photochem. Photobiol. 30, 63 (1979)
[2]. R. Curci, et al. J. Org. Chem. 45, 4758 (1980)

After allowing the mixture to settle, the aqueous layer was decanted off and the organic layer, which contained insoluble salts, were filtered through paper with suction. The filtered solids were washed with CH$_2$Cl$_2$ (1.9 L) and the aqueous layer extracted with this filtrate. The filtered solids were again washed with CH$_2$Cl$_2$ (3.15 L) and the aqueous layer extracted with this filtrate. The combined CH$_2$Cl$_2$ layers were extracted with a solution of KOH (593.3 g) in water (6.31 L)—gentle heating to about 40° C. is often required to dissolve a solid which may separate during the base extraction. The CH$_2$Cl$_2$ layer was then extracted with a solution of KOH (99 g) in water (1.5 L) and the combined base extracts treated with glycine (481.7 g; 6.416 mol; 0.95 eq); the organic layer was discarded.

The solution pH was adjusted to 11.5 with 25% aqueous KOH then heated to boiling. Approximately 900 mL of low boiling liquid (acetone and water) was distilled off until the vapor temperature reached 99° C., following which, the mixture was refluxed for 2 hours. After cooling, the reaction mixture was extracted with CH$_2$Cl$_2$ (3.15 L), the CH$_2$Cl$_2$ phase discarded and the aqueous phase evaporated to dryness under reduced pressure with a 70° C. bath. The residue was boiled in 95% EtOH (8.83 L) for 30 minutes, then allowed to cool slowly with stirring, whereupon the product separates as fine crystals. These were filtered, washed with fresh 95% EtOH (1.26 L) and dried in a 50°–60° C. oven to give the title compound (1.77 kg; 74.6%) as white crystals with mp=120°–2° C. (uncorrected).

IR (KBr) cm$^{-1}$ 3240 (br.), 1590 (br.), 1410, 1130, 710; $^1$H NMR (D$_2$O-TSP) δ 3.1 (s, 2H), 3.89 (d, |J$_{AB}$|=4, 1H) and 4.52 (d, |J$_{AB}$|=4, 1H) [center of pattern: 4.21; ΔV$_{AB}$=18.83 Hz.], 4.68 (s, 6H, exchangeable protons), 7.4 (s, 5H); TLC Rf=0.59 (EtOH:1M triethylammonium bicarbonate, 7:3).

Anal. Calc. for C$_{11}$H$_{15}$NO$_7$K$_2$: C, 37.59; H, 4.30; N, 3.99. Found: C, 37.22; H, 4.24; N, 3.96.

N-acetyl-3-acetoxy-5-phenylpyrrole (2)

A suspension of 2-hydroxy-3-(carboxymethylamino)-hydrocinnamic acid dipotassium salt dihydrate (1) (1.0 kg; 2.87 mol) in pyridine (3.0 L) was treated with acetic anhydride (4.0 L) at ambient temperature under an inert gas atmosphere. A mild exothermic reaction ensued and the reaction temperature rose exponentially to 60°–70° C. during a period of 1.5–2.5 hours. Once the reaction began to cool the mixture was heated to 120°–123° C. for 15 minutes, then allowed to cool to ambient temperature over 1 hour, during which time pyridinium acetate separated as crystals. The mixture was filtered through paper with suction and the salts washed with EtOAc until colorless; the filtrate was evaporated to dryness in vacuo.

The dark red residue was dissolved in EtOAc (3.0 L) washed three times with water (1.0 L)each), dried over MgSO$_4$ and treated with Darco-G60® activated carbon (ICI Americas, Inc.) (300 g). After stirring for 30 minutes the mixture was filtered through Celite® (Johns-Manville) and evaporated to dryness in vacuo to give a reddish-orange oil. This oil was dissolved in warm 2-propanol (1.2 L), then allowed to cool slowly to ambient temperature overnight, whereupon a solid separates. The crystalline product was filtered, washed with 50% aqueous 2-propanol and dried in vacuo to give the title compound (417 g; 60%) with mp=58°–60° C. (uncorrected). A portion was taken up in Et$_2$O, treated with Norit 211, filtered and concentrated under reduced pressure; on standing at 0° C. colorless tiny needles separated. These were filtered, washed with Et$_2$O: Hexane (1:1) and vacuum dried to give the analytical sample with mp=60°–62.5° C. (uncorrected).

IR (CHCl$_3$) cm$^{-1}$ 3020, 1760, 1730, 1595, 1378, 1320, 1220 (br.), 1030, 960, 903; $^1$H NMR (CDCl$_3$) δ 2.23 (s, 3H), 2.27 (s, 3H), 6.18 (d, J=2, 1H), 7.35 (s, 5H) 7.42 (d, J=2, 1H); TLC Rf=0.56 (toluene:diosane, 4:1).

Anal. Calc. for C$_{14}$H$_{13}$NO$_3$: C, 69.12; H, 5.38; N, 5.76. Found: C, 68.88; H, 5.25; N, 5.53.

3-Hydroxy-5-phenylpyrrole (3)

A finely divided portion of N-acetyl-3-acetoxy-5-phenylpyrrole (2) (36.8 g; 0.15 mol) was freed of oxygen by stirring in a flowing argon stream for 10 minutes, then suspended in deoxygenated MeOH (379 mL), cooled to −6° C. (in a −15° C. methanol (MeOH)/dry-ice bath) under an inert gas atmosphere and rapidly treated with an ice cold deoxygenated solution of 2N NaOH (300 mL). The reaction temperature rose immediately upon addition of base to 18° C., and after ~3 minutes the reaction mixture became homogeneous. As the reaction mixture cooled, compound 3 separates as fine crystals. After 15 minutes a solution of cold deoxygenated 2M citric acid (150 mL) was added, the resulting mixture was stirred for 10 minutes, and then filtered. The solid was washed thoroughly with deoxygenated water (200 mL), taking care to minimize exposure of the product to air, then dried under vaccum overnight to yield the title compound (22.3 g; 93.6%) as light pink tiny needles.

IR (KBr) cm$^{-1}$ 3400, 3110, 2900, 1600, 1580, 1555, 1480, 1268, 1180, 742, 640; $^1$H NMR (DMSO-D$^6$) δ 6.1 (m, 1H), 6.3 (m, 1H), 7.0–7.7 (m, 5H), 8.0 (s, 1H), 10.4 (br s, 1H); TLC Rf=0.20–0.28 (EtOH:CHCl$_3$, 1:9).

Anal. Calcd. for C$_{10}$H$_9$NO: C, 75.45; H, 5.70; N, 8.80. Found: C, 75.30; H, 5.69; N, 8.67.

3-(N-tosyl-L-alaninyloxy)-5-phenylpyrrole (4)

A solution of anhydrous tetrahydrofuran (THF, 450 mL), pyridine (43.8 mL; 0.542 mol; 1.2 eq) and trifluoroacetic acid (85.0 mL; 1.10 mol; 2.4 eq), maintained at 0° C. under an inert gas atmosphere, was treated in one portion with 3-hydroxy-5-phenylpyrrole (3) (71.5 g; 0.45 mol; 1.0 eq) followed immediately by the dropwise addition, over 5–10 minutes of a solution of freshly prepared N-tosyl-L-alaninyl chloride (141.0 g; 0.54 mol; 1.2 eq) in anhydrous THF (450 mL). The resulting mixture was stirred for 15 minutes at 0° C. The reaction was then quenched by addition of a solution of 1.0M aqueous citric acid (315 mL) and EtOAc (1.35 L). After brief mixing the phases were separated and the organic layer washed with a solution of aqueous NaCl (360 mL; 0.18 g NaCl per mL of water). The organic layer was next extracted twice with a solution of 5% aqueous NaHCO$_3$ (1.35 L each), and then washed with another portion of aqueous NaCl (360 mL; 0.18 g NaCl per mL of water). The reddish brown organic layer was stirred at ambient temperature for 15 minutes with MgSO$_4$ (101 g) and Darco-G60 (143 g), then filtered through Celite and evaporated to dryness in vacuo from a 37° bath to give (4) as a pinkish-white solid. The crude product was ground to a powder and dissolved in warm (50° C.) THF (250 mL), stirred vigorously and diluted with n-hexane (250 mL). The stirring was continued for 1 hour at ambient temperature as the product crystallized. The solid was filtered, washed with toluene (about 1.0 L) until the filtrate was colorless, then dried in vacuo overnight to yield the title compound (112 g; 65%) as a white powder with mp=154.5°–155° C.

IR (KCl) cm$^{-1}$ 3350, 3325, 1760, 1508, 1320, 1155, 770; $^1$H NMR (DMSO-d$^6$) δ 1.33 (d, J=7, 3H), 2.36 (s, 3H), 4.13 (p, J=8, 1H), 6.25 (m, 1H), 6.73 (m, 1H), 7.05–7.50 (m, 5H), 7.5–7.85 (m, 4H) 8.42 (d, J=8, 1H), 11.18 (br s, 1H); $^{13}$C NMR (DMSO-d$^6$) ppm 18.335, 21.001, 51.370, 98.061, 108.336, 123.423, 126.024, 126.610, 128.560, 128.756, 129.601, 132.397, 137.600, 138.380, 142.737, 169.919; [α]$_D$=−70° (c=1.11, MeOH); TCL Rf=0.45 (EtOAc:hexane, 1:1); TLC Rf=0.40 (toluene:dioxane, 4:1).

Anal. Calcd. for C$_{20}$H$_{20}$N$_2$O$_4$S: C, 62.48; H, 5.24; N, 7.29. Found: C, 62.62; H, 5.27; N, 7.30.

6.3 Synthesis of 3-(N-tosyl-L-alaninyloxy)-1-methyl-5-phenylpyrrole (8)

The synthesis of 3-(N-tosyl-L-alaninyloxy)-1-methyl-5-phenylpyrrole (8) is illustrated in the following reaction sequence:

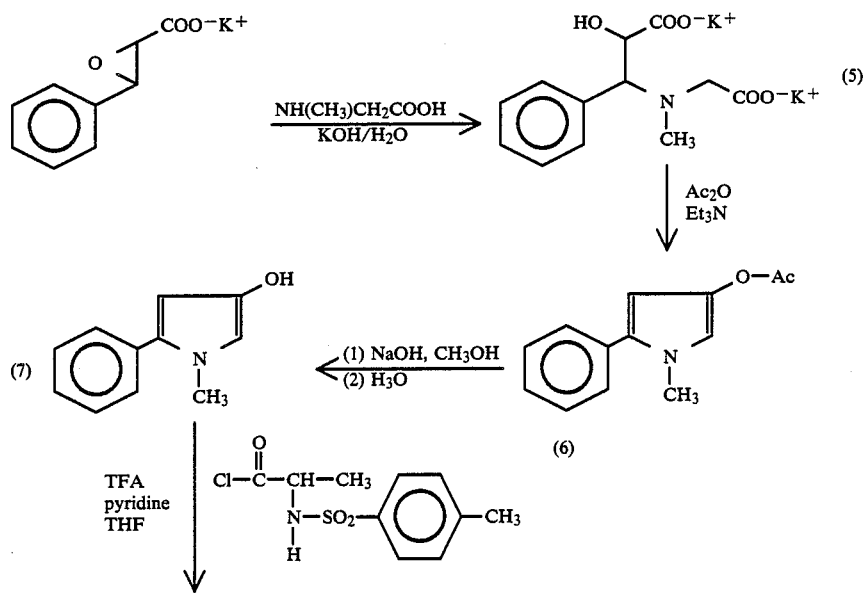

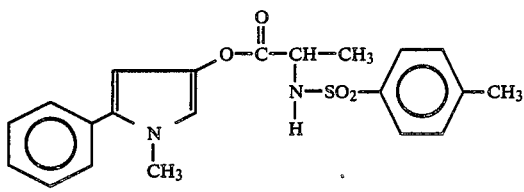

(8)

2-Hydroxy-3-(N-methylcarboxymethylamino)-hydrocinnamic acid dipotassium salt (5)

A mixture of β-phenylglycidic acid potassium salt (30 g; 0.15 mole), N-methylglycine (13.2 g; 0.15 mole), distilled water (119 mL) and KOH solution (9N; 22.3 mL) was heated to reflux for 3 hours to give a light yellow solution. The reaction mixture was evaporated to dryness under reduced pressure at 70° C. The residue was then crystallized from 95% EtOH (100 mL) to give a white solid which, after drying overnight under reduced pressure at 110° C., yielded 30.8 g of white solid (5) yield 63%.

IR (KCl) cm$^{-1}$ 3360 (br.), 1580, 1405, 705; $^1$H NMR (CD$_3$OD) δ 2.30 (s, 3H), 2.98 (s, 2H), 3.70 (d, J=3 Hz, 1H), 4.48 (d, J=3 Hz, 1H), 4.92 (s, 1H), 7.40 (s, 5H); TLC Rf=0.51 (EtOH:1M triethylammonium bicarbonate, 7:3). (Product had no melting point less than 270° C.).

3-Acetoxy-N-methyl-5-phenylpyrrole (6)

A mixture of 2-hydroxy-3-(N-methylcarboxymethylamino)-hydrocinnamic acid dipotassium salt (5) (15.2 g, 46 mmole), acetic anhydride (173 mL) and triethylamine (308 mL) was heated at 90° C. for 19 hrs. The reaction mixture, which became deep brown in color, was filtered and the solid washed with ether. The filtrate was evaporated under reduced pressure to give a deep brown residue, which was taken up in ether (300 ml) and water (200 ml). The layers were separated and the ether layer washed with another portion of water (200 ml). The ether solution was then dried over MgSO$_4$, filtered and concentrated under reduced pressure to give 10.7 g of brown residue which was purified by evaporative distillation (120°–135° C.; 0.03 torr) and crystallization from ether yielded 3.0 g of white crystals (6) (yield 30%) mp=64°–65° C.

IR (CHCl$_3$) cm$^1$ 2990, 1750, 1570, 1518, 1482, 1375, 1240 (br.), 1024, 910, 700; $^1$H NMR (CDCl$_3$) δ 2.20 (s, 3H), 3.58 (s, 3H), 6.10 (d, J=2 Hz, 1H), 6.75 (d, J=2 Hz, 1H), 7.35 (s, 5H); TLC Rf=0.58 (Hexane:EtOAc 7:3).

Anal. Calcd. for C$_{13}$H$_{13}$NO$_2$: C, 72.54; H, 6.10; N, 6.44; Found: C, 72.57; H, 6.09; N, 6.51.

3-(N-tosyl-L-alaninyloxy)-1-methyl-5-phenylpyrrole (8)

To a mixture of deoxygenated methanol (15.5 ml) and 3-acetoxy-1-methyl-5-phenylpyrrole (5) (1.3 g, 6.2 mmole), under argon, was added deoxygenated NaOH (2N, 12.5 ml). The reaction mixture was stirred in an icebath for 15 minutes. Then deoxygenated citric acid (2M, 7 ml) was added and the resulting mixture was stirred and an ice bath for 8 minutes. The reaction mixture was concentrated under reduced pressure, then 20 ml of water was added and was extracted twice with ethylacetate (EtOAc) (50 ml). The EtOAc layers were combined, dried over MgSO$_4$, filtered and concentrated under reduced pressure to give 3-hydroxy-N-methyl-5-phenylpyrrole (7) as an orange residue. Under argon, a cold solution of anhydrous THF (12.4 ml), pyridine (0.6 ml, 7.4 mmole, 1.2 eq) and trifluoroacetic acid (1.2 ml, 15 mmole, 2.4 eq) was added to the orange residue, followed immediately by the addition of a solution of freshly prepared N-tosyl-L-alaninyl chloride (1.2 g, 7.4 mmole, 1.2 eq) in anhydrous THF 12.4 ml). The resulting mixture was stirred for one hr at 0° C. Then the reaction was quenched by the addition of aqueous citric acid (1M, 5 ml) and EtOAc (30 ml). After a brief mixing, the layers were separated and the organic layer was successively washed with saturated NaCl solution, twice with 5% NaHCO$_3$ solution and again with saturated NaCl solution. the EtOAc extract was then dried over MgSo$_4$, treated with Norit 211, filtered and concentrated under reduced pressure to give the crude product (8) as an orange residue. This was dissolved in hexane:EtOAc (1:1) (5 mL) and chromatographed on a column (SiO$_2$, 100 g) by elution with hexane:EtOAc (7:3) to give 1 g of (8) as a thick light orange oil. A portion of this crude product was further purified by semi-preparative HPLC (column, IBM silica, 1 cm×25 cm; mobile phase, hexane:EtOAc 8:2; flow rate, 4.0 ml/min; pressure, 0.2 psi) to yield a honey color thick oil (8)

IR (film) cm$^{-1}$ 3260, 2950, 1760, 1520, 1350, 1170, 770; $^1$H NMR (DMSO-d$_6$) δ 1.28 (d, J=7 Hz, 3H), 2.36 (s, 3H), 3.58 (s, 3H), 5.85 (d, J=2 Hz, 1H), 6.15 (m, 1H), 6.74 (d, J=2 Hz, 1H), 7.30-7.80 (m, 9H), 8.37 (d, J=8 Hz, 1H); $^{13}$C NMR (DMSO-d$_6$) δ 18.205, 20.936, 34.917, 51.240, 100.598, 113.148, 126.544, 127.00, 128.105, 128.560, 129.601, 130.901, 132.202, 135.714, 138.315, 142.672, 169.724; TLC Rf=0.52 (toluene:dioxane 4:1), High-resolution mass spectrum, C$_{21}$H$_{22}$N$_2$O$_4$S requires m/e 398.1300, found m/e 398.1297.

6.4 Synthesis of 3-(N-tosyl-L-alaninyloxy)-5-(p-chlorophenyl)pyrrole (13)

The synthesis of 3-(N-tosyl-L-alaninyloxy)-5-(p-chlorophenyl)pyrrole (13) is illustrated in the following reaction sequence:

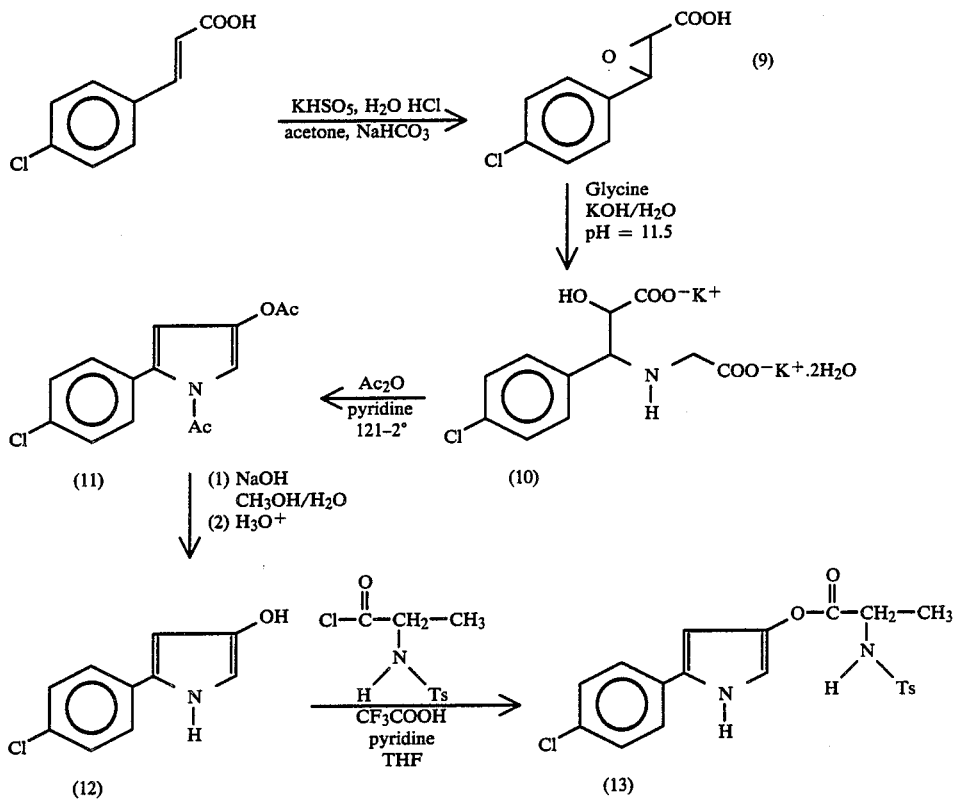

trans-β-(p-Chlorophenyl)glycidic acid (9)

To a stirred slurry of p-chlorocinnamic acid (68.5 g; 0.375 mol) in 260 mL of acetone was added NaHCO$_3$ (137 g; 1.63 mol), followed by slow addition of 260 mL of water. To this mixture was added, over 2.5 hours at 22°–27° C., a mixture of OXONE (211 g; 0.343 mol), 120 mg of disodium EDTA and 805 mL of water. After five hours the mixture was acidified with 70 mL of cold 12N HCl, to bring the pH down to about 2.5, and it then extrated with 700 mL of ethyl acetate. The extract was washed with brine, dried with MgSO$_4$, filtered, and the filtrate was evaporated to dryness under vacuum. The white solids were crystallized from ethyl acetate: mp 121°–5° C. (72.2 g; 97% yield). $^1$H NMR (CDCl$_3$/DMSO-D$_6$) δ (m, 4H), 4.05 (d, J=2, 1H), and 3.4 (d, J=2, 1H).

Anal. Calcd. for C$_9$H$_7$ClO$_3$: C, 54.43; H, 3.55; Cl, 17.85. Found: C, 54.53; H, 3.80; Cl, 17.91.

2-Hydroxy-3-(carboxymethylamino)-p-chlorohydrocinnamic acid dipotassium salt dihydrate (10)

To a solution of KOH (85%) 46.7 g; 0.709 mol) and 400 mL of water was added glycine (25.9 g; 0.345 mol) followed by trans-β-p-chlorophenylglycidic acid (9) (72.2 g; 0.3635 mol). This mixture was heated at 100° C. for two hours, cooled to room temperature and sufficient KOH added to raise the pH to 12. The turbid solution was extrated three times with ethyl acetate, which extract was then discarded; the clear aqueous solution (about 500 mL) was evaporated under vacuum to dryness using a 70° water bath. The solids were then dissolved in about 350 mL of hot ethanol, filtered, and the filtrate chilled in an ice bath for several hours. The crystallized solids were collected by filtration and washed with some cold ethanol: mp 93°–5° C. with decarboxylation at 185° C. (57.2 g; 41%).

$^1$H NMR (D$_2$O-TSP) δ 7.4 (s, 4H), 4.4 (d, J=4, 1H), 4.05 (d, J=4, 1H), and 3.1 (s, 2H).

Anal. Calcd. for C$_{11}$H$_{10}$ClNO$_5$K$_2$.2H$_2$O: C, 34.24; H, 3.66; N, 3.63. Found: C, 34.40; H, 4.03; N, 3.42.

N-acetyl-3-acetoxy-5-(p-chlorophenyl)pyrrole (11)

To the 2-hydroxy-3-(carboxymethylamino)-p-chlorohydrocinnamic acid dipotassium salt dihydrate (10) (10 g; 0.02591 mol) was added acetic anhydride (40 mL) and pyridine (30 mL). This mixture was gently heated to 35° C. at which point the solution exothermed to 67°, then began to cool, whereupon heating was again resumed. The mixture was heated at 121°–2° (internal temperature) for one hour then cooled. To the reaction mixture was added about 30 mL of ethyl acetate which precipitated most of the pyridinium acetate salt; this salt was collected by filtration and washed with a small amount of ethyl acetate. The filtrate was then evaporated under vacuum to an oil and ice water added. The product was extracted with ether and the ether extracts were successively washed twice with cold dilute citric acid, cold water, three times with cold dilute aq. NaHCO$_3$, cold water and brine, followed by drying over MgSO$_4$ and filtering. The filtrate was treated with 10 g of Darco, stirred for 20 minutes and then filtered. The filtrate was evaporated under vacuum to an oil. To the oil was added 25 mL of 2-propanol. The resultant solution yielded, with chilling and scratching, pale yellow crystals: mp 69°–71° C. (3.4 g; 47%); TLC RF=0.61 (toluene:dioxane, 95:5). An analytical sample was recrystallized from 2-propanol but no change in mp was observed.

IR (KCl) cm$^{-1}$ 1755 (C=O, ester) and 1730 (C=O, amide); $^1$H NMR (CDCl$_3$) δ 7.4 (m, 5H), 6.2 (d, J=2, 1H), 2.4 (s, 3H) and 2.3 (s, 3H).

Anal. Calcd. for C$_{14}$H$_{12}$ClNO$_3$: C, 60.55; H, 4.36; N, 5.04. Found: C, 60.65; H, 4.55; N, 5.07.

3-Hydroxy-5-(p-chlorophenyl)pyrrole (12)

A sample of N-acetyl-3-acetoxy-5-p-chlorophenyl-pyrrole (11) (2.8 g; 0.01 mol) was deoxygenated for ten minutes with a stream of N$_2$. The solids were then dissolved in deoxygenated methanol (30 mL) which was then chilled to −8° C. At once was added a cold deoxygenated solution of NaOH (1.6 g; 0.04 mol) in 20 mL H$_2$O, which solution was then heated briefly to 15° C. and then immediately cooled to −5° C.; after 25 minutes the clear solution was treated with a cold deoxygenated solution of citric acid (4.2 g; 0.02 mol) in 15 ml H$_2$O. The temperature rose briefly to 5° C. After 0.5 hour of stirring at −5° the solids were collected by filtration and washed with cold deoxygenated H$_2$O. The pale green product was dried under vacuum at room temperature over P$_2$O$_5$ for several days (1.3 g; 68%); TLC Rf=0.19 (CHCl$_3$:EtOH, 9:1); IR (KCL) showed no evidence for C=O absorption.

Anal. Calcd. for C$_{10}$H$_8$ClNO.1/6H$_2$O: C, 61.08; H, 4.27; N, 7.12. Found: C, 61.36; H, 4.44; N, 6.85.

3-(N-tosyl-L-alaninyloxy-5-(-chlorophenyl)pyrrole (13)

To N$_2$ deoxygenated THF (15 mL) was added pyridine (0.65 mL; 0.008 mol), trifluoroacetic acid (1.27 mL; 0.0164 mol), and 3-hydroxy-5-p-chlorophenylpyrrole (12) (1.3 g; 0.0065 mol). The solution was chilled to 0° C. to −4° C. and a N$_2$ deoxygenated chilled (0° to −4° C.) solution of N-tosyl-L-alaninyl chloride (2.1 g; 0.008 mol) in 15 mL of THF was added over 10 minutes. After maintaining the mixture at 0° C. for one hour, a mixture of ice and 100 mL of 1N citric acid was added. This mixture was extracted with ethyl acetate and the extract washed once with cold brine, twice with cold dilute NaHCO$_3$, and once with cold brine, following which, it was dried over MgSo$_4$ and filtered. The filtrate was treated with 2 g of Darco and stirred for ten minutes, filtered and the filtrate concentrated under vacuum to a reddish-brown oil. A second treatment with 1.3 g Darco afforded a light reddish oil. This oil was dissolved in toluene:cyclohexane (4:1) and placed in the refrigerator overnight. Light salmon crystals were obtained (1.45 g; 53%); mp 113°–5° C.; TLC Rf=0.47 (ET$_2$O); IR (kCl) cm$^{-1}$ 1740 (C=O, ester); $^1$H NMR (CDCl$_3$) δ 8.4 (br. s, 1H), 7.8–7.2 (m, 8H), 6.7 (m, 1H), 6.2 (m, 1H), 5.5 (d, J=9, 1H), 4.2 (p, J=8, 1H), 2.4 (d, 3H), 1.4 (d, 3H); MS (EI, DIP) m/e 418 (M+, 2.3%) and 420 (M+, 0.8%).

Anal. Calcd. for C$_{20}$H$_{19}$ClN$_2$O$_4$S: C, 57.34; H, 4.57; N, 6.69. Found: C, 57.53; H, 4.58; N, 6.67.

6.5 Preparation of indoxyl-N-tosyl-L-alaninate

A series of experiments was conducted to study the esterification of indoxyl utilizing various organic acids to direct the acylation to the hydroxyl group in preference to the nitrogen. The reaction, and possible N- and O-acylation products, can be depicted by:

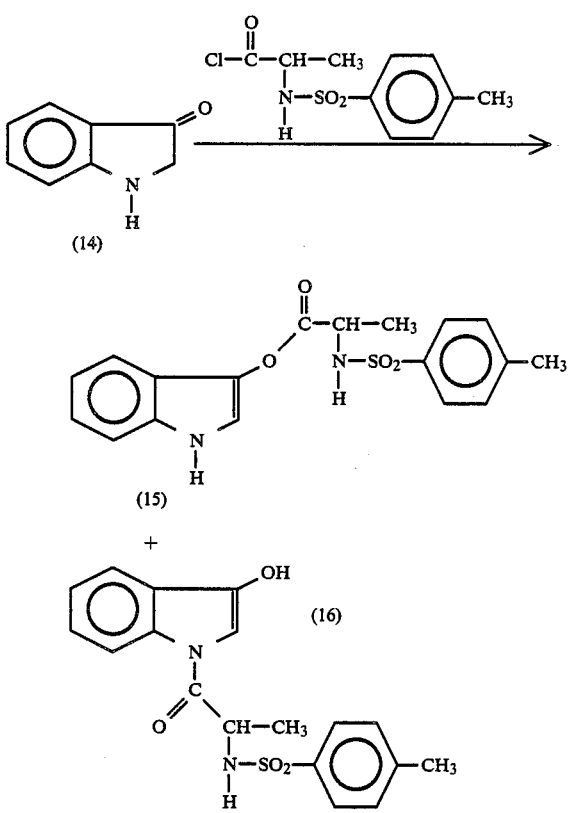

The following experiments show that the presence of organic acid directs the acylation principally to the hydroxyl group to produce the desired product (15), with minimal N-acylation (16).

6.5.1 Use of Citric Acid

A stirred cold (−25° C.) mixture of 1.33 g (10 mmol) of indoxyl (14), 3.6 of pyridine, 27 ml of dry THF, 0.6 g (3 mmol) of anhydrous citric acid and 1.2 g of anhydrous MgSO$_4$ was treated dropwise (under argon) with a solution of 3.93 g (15 mmol) of N-tosyl-L-alaninyl chloride in 15 mL of THF, over a period of 1 hr. HPLC analysis showed a 31% conversion to the desired ester. (15)

6.5.2 Use of Oxalic Acid

A cold (0° C.) stirred mixture of 3.0 g (22.5 mmol) of indoxyl (14), 7.2 mL of pyridine, 54 mL of dry THF, 0.9 g (10 mmol) of oxalic acid and 1.2 g of MgSO$_4$ was treated dropwise (under argon) with 8.64 g (33 mmol) of N-tosyl-L-alaninyl chloride, dissolved in 30 mL of dry THF, over a period of 30 min. After 1 hr at 0° C. HPLC analysis shows a 57.5% yield of (15)

6.5.3 Use of Trifluoroacetic Acid

To a cold (0° C.) stirred mixture of 594 mL of pyridine, 35 g of MgSO$_4$, 1320 mL of THF and 107 mL of trifluoroacetic acid, under argon, was added 167 g (1 mole of 79% pure) of indoxyl (14) followed immediately by the rapid addition of 392.6 g (1.5 mol) of the N-tosyl-L-alanininyl chloride dissolved in 880 mL of THF at such an addition rate as to keep the reaction temperature below 10° C. The mixture was stirred at 0° C. for 1.5 hr then at room temperature for 1 hr. The volatiles were removed on the rotary evaporator at 45° C. The dark viscous residue was partitioned between 2 L of ethyl acetate and 2 L of cold 1N citric acid, filtered through activated charcoal to break the emulsion, and the layers separated. The ethyl acetate phase was washed twice with 1 L portions of 1N citric acid, then twice with 1 L portions of saturated brine, three times with 1 L portions of 5% sodium bicarbonate solution, and finally twice with 2 L portions of brine. The organic phase was dried (CaCl$_2$), filtered and evaporated. The dark viscous residue was dissolved in 4 L of ether, 500 g of Darco-G60 added, filtered through 300 g of Darco G-60, filter cake washed with 2 L of ether, and the filtrate evaporated to a dark viscous oil. The oil was crystallized from 500 mL of toluene to give 270 g (75% yield) of 15 mp 99°-101° C. Recrystallization from hot toluene gave 243.2 g (68%) mp 101.5°-5° C.

Anal. calcd for C$_{18}$H$_{18}$N$_2$O$_4$S: C, 60.32; H, 5.06; N, 7.82. Found: C, 59.74; H, 5.26; N, 7.90.

6.5.4 Use of CH$_2$Cl$_2$ as Solvent

A cold (0° C.) stirred mixture of 217 g (20 mmol) of 14, 25 mL of dry dichloromethane, 7.2 mL of dry pyridine, and 1.8 mL of trifluoroacetic acid was treated dropwise (under argon) with 7.68 g (30 mmol) of N-tosyl-L-alaninyl chloride, dissolved in 20 mL of dry dichloromethane over a 10 min. period. The mixture was stirred for 30 min. at 5° C. then for 1 hr at 25° C. The mixture was washed with a saturated sodium bicarbonate and brine then dried (MgSO$_4$), filtered and evaporated. The residue was dissolved in ether, decolorized with charcoal, filtered and evaporated. Crystallization from toluene gave 2.54 g (36%) of 15 mp 96°-98° C.

6.5.5 Use of Diisopropylethylamine

A stirred cold (0° C.) mixture of 3.35 g (25 mmol) of 1, 5.1 g (39 mmol) of disopropylethylamine, 80 Ml of dry THF, and 1 g of anhydrous MgSO$_4$ was treated dropwise (under argon) with 9.81 g (37.5 mmol) of N-tosyl-L-alaninyl chloride dissolved in 30 mL of dry THF, over a period of 20 min. HPLC analysis indicated an 80% yield of 3-hydroxy-1-(N-p-tosylsulfonyl)alaninyl indole (16) (HPLC retention time 10.5 min.) with only a trace of 15 being formed. Thus, the absence of an organic acid resulted in only a trace of the desired ester.

6.5.6 Use of Pyridine

A stirred cold (0° C.) mixture of 3.35 g (25 mmol) of 14, 8 Ml (100 mmol) of dry pyridine, 80 Ml of dry THF, and 1 g of anhydrous MgSO$_4$ (1 g) was treated dropwise (under argon) with 9.81 (37.5 mmol) of N-tosyl-L-alaninyl chloride dissolved in 30 mL of dry THF, over a period of 20 min. HPLC analysis indicated an 80% of 16 and only a trace of 15. The absence of an organic acid resulted in only a trace of the desired ester.

What is claimed is:

1. The method of preparing the compound 3-(N-tosyl-L-alaninyloxy)-5-phenylpyrrole which consists essentially of reacting 3-hydroxy-5-phenylpyrrole and N-tosyl-L-alaninylchloride in the presence of a solvent used for esterification, said solvent being selected from the group consisting of tetrahydrofuran, methylene chloride, chloroform, acetone, diethylether and benzene; a weak organic base selected from the group consisting of pyridine and 2,6-lutidine; and about 2.4 equivalents of trifluoroacetic acid based on about 1.2 equivalent of N-tosyl-L-alaninylchloride.

2. The method of preparing the compound 3-(N-tosyl-L-alaninyloxy)-1-methyl-5-phenylpyrrole which consists essentially of reacting 3-hydroxy-N-methyl-5-phenylpyrrole and N-tosyl-L-alaninylchloride in the presence of a solvent for the esterification selected from the group consisting of tetrahydrofuran, methylene chloride, chloroform, acetone, diethylether and benzene; a weak organic base selected from the group consisting of pyridine and 2,6-lutidine; and about 2.4 equivalents of trifluoroacetic acid based on about 1.2 equivalents of N-tosyl-L-alaninylchloride.

3. The method of preparing the compound 3-(N-tosyl-L-alaninyloxy)-5-(p-chlorophenyl)pyrrole which consists essentially of reacting 3-hydroxy-5-(p-chlorophenyl)pyrrole and N-tosyl-L-alaninylchloride in the presence of a solvent for esterification selected from the group consisting of tetrahydrofuran, methylene chloride, chloroform, acetone, diethylether and benzene; a weak organic base selected from the group consisting of pyridine and 2,6-lutidine; and about 2.4 equivalents of trifluoroacetic acid based on about 1.2 equivalents of N-tosyl-L-alaninylchloride.

4. The method of claim 1 in which the reaction is performed in the presence of pyridine and trifluoroacetic acid, the molar ratio of pyridine to acid being up to about 4:1.

5. The method of claim 2 in which the reaction is performed in the presence of pyridine and trifluoroacetic acid, the molar ratio of pyridine to acid being up to about 4:1.

6. The method of claim 3 in which the reaction is performed in the presence of pyridine and trifluroacetic acid, the molar ratio of pyridine to acid being up to about 4:1.

* * * * *